(12) United States Patent
Bykanov et al.

(10) Patent No.: US 7,355,191 B2
(45) Date of Patent: Apr. 8, 2008

(54) SYSTEMS AND METHODS FOR CLEANING A CHAMBER WINDOW OF AN EUV LIGHT SOURCE

(75) Inventors: Alexander N. Bykanov, San Diego, CA (US); William F. Marx, San Diego, CA (US)

(73) Assignee: Cymer, Inc., San Diego, CA (US)

( * ) Notice: Subject to any disclaimer, the term of this patent is extended or adjusted under 35 U.S.C. 154(b) by 262 days.

(21) Appl. No.: 11/288,868

(22) Filed: Nov. 28, 2005

(65) Prior Publication Data
US 2006/0097203 A1    May 11, 2006

Related U.S. Application Data

(63) Continuation-in-part of application No. 11/174,442, filed on Jun. 29, 2005, now Pat. No. 7,196,342, and a continuation-in-part of application No. 11/067,099, filed on Feb. 25, 2005, now Pat. No. 7,109,503, which is a continuation-in-part of application No. 10/979,945, filed on Nov. 1, 2004.

(51) Int. Cl.
*G01J 3/10* (2006.01)

(52) U.S. Cl. .............................. 250/504 R; 250/503.1; 250/251; 378/119; 378/34; 378/143

(58) Field of Classification Search ...................... None
See application file for complete search history.

(56) References Cited

U.S. PATENT DOCUMENTS 2,759,106 A    8/1956   Wolter ........................ 250/50
3,150,483 A    9/1964   Mayfield et al. ............. 60/35.5
3,232,046 A    2/1966   Meyer ......................... 50/35.5
3,279,176 A    10/1966  Boden ......................... 60/202
3,746,870 A    7/1973   Demarest ..................... 250/227
3,960,473 A    6/1976   Harris ........................ 425/467

(Continued)

FOREIGN PATENT DOCUMENTS

JP          02-105478          4/1990

(Continued)

OTHER PUBLICATIONS

Andreev et al., "Enhancement of laser/EUV conversion by shaped laser pulse interacting with Li-contained targets for EUV lithography," Proc. of SPIE 5196:128-136 (2004).

(Continued)

*Primary Examiner*—Jack I. Berman
*Assistant Examiner*—Zia R. Hashmi
(74) *Attorney, Agent, or Firm*—Matthew K. Hillman

(57) ABSTRACT

Systems and methods are disclosed for cleaning a chamber window of an extreme ultraviolet (EUV) light source. The window may have an inside surface facing a chamber interior and an opposed outside surface and the light source may generate debris by plasma formation. For the system, a subsystem may be positioned outside the chamber and may be operable to pass energy through the window to heat debris accumulating on the inside surface of the window. In a first embodiment, the subsystem may place a flowing, heated gas in contact with the outside surface of the window. In another embodiment, electromagnetic radiation may be passed through the window.

23 Claims, 6 Drawing Sheets

U.S. PATENT DOCUMENTS

| | | | |
|---|---|---|---|
| 3,961,197 A | 6/1976 | Dawson | 250/493 |
| 3,969,628 A | 7/1976 | Roberts et al. | 250/402 |
| 4,042,848 A | 8/1977 | Lee | 313/231.6 |
| 4,088,966 A | 5/1978 | Samis | 313/231.5 |
| 4,143,275 A | 3/1979 | Mallozzi et al. | 250/503 |
| 4,162,160 A | 7/1979 | Witter | 75/246 |
| 4,203,393 A | 5/1980 | Giardini | 123/30 |
| 4,223,279 A | 9/1980 | Bradford, Jr. et al. | 331/94.5 |
| 4,364,342 A | 12/1982 | Asik | 123/143 |
| 4,369,758 A | 1/1983 | Endo | 123/620 |
| 4,455,658 A | 6/1984 | Sutter et al. | 372/38 |
| 4,504,964 A | 3/1985 | Cartz et al. | 378/119 |
| 4,507,588 A | 3/1985 | Asmussen et al. | 315/39 |
| 4,534,035 A | 8/1985 | Long | 372/85 |
| 4,536,884 A | 8/1985 | Weiss et al. | 378/119 |
| 4,538,291 A | 8/1985 | Iwamatsu | 378/119 |
| 4,550,408 A | 10/1985 | Karning et al. | 372/58 |
| 4,561,406 A | 12/1985 | Ward | 123/536 |
| 4,596,030 A | 6/1986 | Herziger et al. | 378/119 |
| 4,618,971 A | 10/1986 | Weiss et al. | 378/34 |
| 4,626,193 A | 12/1986 | Gann | 431/74 |
| 4,633,492 A | 12/1986 | Weiss et al. | 378/119 |
| 4,635,282 A | 1/1987 | Okada et al. | 378/34 |
| 4,751,723 A | 6/1988 | Gupta et al. | 378/119 |
| 4,752,946 A | 6/1988 | Gupta et al. | 378/119 |
| 4,774,914 A | 10/1988 | Ward | 123/162 |
| 4,837,794 A | 6/1989 | Riordan et al. | 378/119 |
| 4,891,820 A | 1/1990 | Rando et al. | 372/93 |
| 4,928,020 A | 5/1990 | Birx et al. | 307/106 |
| 4,959,840 A | 9/1990 | Akins et al. | 372/57 |
| 5,005,180 A | 4/1991 | Edelman et al. | 372/57 |
| 5,023,884 A | 6/1991 | Akins et al. | 372/57 |
| 5,023,897 A | 6/1991 | Neff et al. | 378/122 |
| 5,025,445 A | 6/1991 | Anderson et al. | 372/20 |
| 5,025,446 A | 6/1991 | Kuizenga | 372/21 |
| 5,027,076 A | 6/1991 | Horsley et al. | 324/674 |
| 5,070,513 A | 12/1991 | Letardi | 372/83 |
| 5,102,776 A | 4/1992 | Hammer et al. | 430/311 |
| 5,126,638 A | 6/1992 | Dethlefsen | 315/326 |
| 5,142,166 A | 8/1992 | Birx | 307/419 |
| 5,175,755 A | 12/1992 | Kumakhov | 378/34 |
| 5,189,678 A | 2/1993 | Ball et al. | 372/28 |
| 5,313,481 A | 5/1994 | Cook et al. | 372/37 |
| 5,315,611 A | 5/1994 | Ball et al. | 372/56 |
| 5,319,695 A | 6/1994 | Itoh et al. | 378/84 |
| 5,359,620 A | 10/1994 | Akins | 372/58 |
| RE34,806 E | 12/1994 | Cann | 427/446 |
| 5,411,224 A | 5/1995 | Dearman et al. | 244/53 |
| 5,448,580 A | 9/1995 | Birx et al. | 372/38 |
| 5,471,965 A | 12/1995 | Kapich | 123/565 |
| 5,504,795 A | 4/1996 | McGeoch | 378/119 |
| 5,729,562 A | 3/1998 | Birx et al. | 372/38 |
| 5,763,930 A | 6/1998 | Partlo | 250/504 |
| 5,852,621 A | 12/1998 | Sandstrom | 372/25 |
| 5,856,991 A | 1/1999 | Ershov | 372/57 |
| 5,863,017 A | 1/1999 | Larson et al. | 248/176.1 |
| 5,866,871 A | 2/1999 | Birx | 219/121 |
| 5,936,988 A | 8/1999 | Partlo et al. | 372/38 |
| 5,953,360 A | 9/1999 | Vitruk et al. | 372/87 |
| 5,963,616 A | 10/1999 | Silfvast et al. | 378/122 |
| 5,970,076 A | 10/1999 | Hamada | 372/20 |
| 5,978,394 A | 11/1999 | Newman et al. | 372/32 |
| 5,991,324 A | 11/1999 | Knowles et al. | 372/57 |
| 6,005,879 A | 12/1999 | Sandstrom et al. | 372/25 |
| 6,016,323 A | 1/2000 | Kafka et al. | 372/38 |
| 6,016,325 A | 1/2000 | Ness et al. | 372/38 |
| 6,018,537 A | 1/2000 | Hofmann et al. | 372/25 |
| 6,028,880 A | 2/2000 | Carlesi et al. | 372/58 |
| 6,031,241 A | 2/2000 | Silfvast et al. | 250/504 |
| 6,031,598 A | 2/2000 | Tichenor et al. | 355/67 |
| 6,039,850 A | 3/2000 | Schulz | 204/192.15 |
| 6,051,841 A | 4/2000 | Partlo | 250/504 |
| 6,064,072 A | 5/2000 | Partlo et al. | 250/504 |
| 6,067,311 A | 5/2000 | Morton et al. | 372/57 |
| 6,094,448 A | 7/2000 | Fomenkov et al. | 372/102 |
| 6,104,735 A | 8/2000 | Webb | 372/37 |
| 6,128,323 A | 10/2000 | Myers et al. | 372/38.1 |
| 6,151,346 A | 11/2000 | Partlo et al. | 372/38 |
| 6,151,349 A | 11/2000 | Gong et al. | 372/58 |
| 6,164,116 A | 12/2000 | Rice et al. | 73/1.72 |
| 6,172,324 B1 | 1/2001 | Birx | 219/121.57 |
| 6,192,064 B1 | 2/2001 | Algots et al. | 372/99 |
| 6,195,272 B1 | 2/2001 | Pascente | 363/21 |
| 6,208,674 B1 | 3/2001 | Webb et al. | 372/57 |
| 6,208,675 B1 | 3/2001 | Webb | 372/58 |
| 6,219,368 B1 | 4/2001 | Govorkov | 372/59 |
| 6,240,117 B1 | 5/2001 | Gong et al. | 372/58 |
| 6,285,743 B1 | 9/2001 | Kondo et al. | 378/119 |
| 6,304,630 B1 | 10/2001 | Bisschops et al. | 378/119 |
| 6,307,913 B1 | 10/2001 | Foster et al. | 378/34 |
| 6,317,448 B1 | 11/2001 | Das et al. | 372/32 |
| 6,359,922 B1 | 3/2002 | Partlo et al. | 372/58 |
| 6,370,174 B1 | 4/2002 | Onkels et al. | 372/38.04 |
| 6,377,651 B1 | 4/2002 | Richardson et al. | 378/34 |
| 6,381,257 B1 | 4/2002 | Ershov et al. | 372/57 |
| 6,392,743 B1 | 5/2002 | Zambon et al. | 355/69 |
| 6,396,900 B1 | 5/2002 | Barbee, Jr. et al. | 378/84 |
| 6,404,784 B2 | 6/2002 | Komine | 372/9 |
| 6,414,979 B2 | 7/2002 | Ujazdowski et al. | 372/87 |
| 6,442,181 B1 | 8/2002 | Oliver et al. | 372/25 |
| 6,452,194 B2 | 9/2002 | Bijkerk et al. | 250/492.2 |
| 6,452,199 B1 | 9/2002 | Partlo et al. | 250/504 |
| 6,466,602 B1 | 10/2002 | Fleurov et al. | 372/87 |
| 6,477,193 B2 | 11/2002 | Oliver et al. | 372/58 |
| 6,493,323 B1 | 12/2002 | Dobrowolski et al. | 378/119 |
| 6,493,374 B1 | 12/2002 | Fomenkov et al. | 372/102 |
| 6,529,531 B1 | 3/2003 | Everage et al. | 372/20 |
| 6,532,247 B2 | 3/2003 | Spangler et al. | 372/61 |
| 6,535,531 B1 | 3/2003 | Smith et al. | 372/25 |
| 6,538,737 B2 | 3/2003 | Sandstrom et al. | 356/334 |
| 6,541,786 B1 | 4/2003 | Partlo et al. | 250/504 |
| 6,549,551 B2 | 4/2003 | Partlo et al. | 372/38.07 |
| 6,566,667 B1 | 5/2003 | Partlo et al. | 250/504 |
| 6,566,668 B2 | 5/2003 | Rauch et al. | 250/504 |
| 6,567,450 B2 | 5/2003 | Myers et al. | 372/55 |
| 6,576,912 B2 | 6/2003 | Visser et al. | 250/492.2 |
| 6,580,517 B2 | 6/2003 | Lokai et al. | 356/519 |
| 6,584,132 B2 | 6/2003 | Morton | 372/57 |
| 6,586,757 B2 | 7/2003 | Melnychuk et al. | 250/504 |
| 6,590,959 B2 | 7/2003 | Kandaka et al. | 378/119 |
| 6,621,846 B1 | 9/2003 | Sandstrom et al. | 372/57 |
| 6,625,191 B2 | 9/2003 | Knowles et al. | 372/55 |
| 6,647,086 B2 | 11/2003 | Amemiya et al. | 378/34 |
| 6,671,294 B2 | 12/2003 | Kroyan et al. | 372/20 |
| 6,721,340 B1 | 4/2004 | Fomenkov et al. | 372/25 |
| 6,744,060 B2 | 6/2004 | Ness et al. | 315/111.01 |
| 6,757,316 B2 | 6/2004 | Newman et al. | 372/57 |
| 6,782,031 B1 | 8/2004 | Hofmann et al. | 372/90 |
| 6,795,474 B2 | 9/2004 | Partlo et al. | 372/57 |
| 6,804,327 B2 | 10/2004 | Schriever et al. | 378/119 |
| 6,815,700 B2 | 11/2004 | Melnychuk et al. | 250/504 |
| 6,822,251 B1 | 11/2004 | Arenberg et al. | 250/504 |
| 6,865,255 B2 | 3/2005 | Richardson | 378/119 |
| 2001/0006217 A1 | 7/2001 | Bisschops | 250/493.1 |
| 2001/0055364 A1 | 12/2001 | Kandaka et al. | 378/119 |
| 2002/0006149 A1 | 1/2002 | Spangler et al. | 372/61 |
| 2002/0009176 A1 | 1/2002 | Ameniya et al. | 378/34 |
| 2002/0012376 A1 | 1/2002 | Das et al. | 372/58 |
| 2002/0014598 A1 | 2/2002 | Melnychuk et al. | 250/504 |
| 2002/0014599 A1 | 2/2002 | Rauch et al. | 250/504 |
| 2002/0048288 A1 | 4/2002 | Kroyan et al. | 372/20 |
| 2002/0100882 A1 | 8/2002 | Partlo et al. | 250/504 |
| 2002/0101589 A1 | 8/2002 | Sandstrom et al. | 356/334 |
| 2002/0105994 A1 | 8/2002 | Partlo et al. | 372/57 |

| | | | |
|---|---|---|---|
| 2002/0114370 A1 | 8/2002 | Onkels et al. ............... | 372/55 |
| 2002/0141536 A1 | 10/2002 | Richardson ................. | 378/119 |
| 2002/0163313 A1 | 11/2002 | Ness et al. ............... | 315/111.01 |
| 2002/0168049 A1 | 11/2002 | Schriever et al. ........... | 378/119 |
| 2003/0006383 A1 | 1/2003 | Melnychuk et al. ........ | 250/504 |
| 2003/0068012 A1 | 4/2003 | Ahmad et al. .............. | 378/119 |
| 2003/0219056 A1 | 11/2003 | Yager et al. .................. | 372/57 |
| 2004/0047385 A1 | 3/2004 | Knowles et al. .............. | 372/55 |

FOREIGN PATENT DOCUMENTS

| | | |
|---|---|---|
| JP | 03-173189 | 7/1991 |
| JP | 06-053594 | 2/1994 |
| JP | 09-219555 | 8/1997 |
| JP | 2000-058944 | 2/2000 |
| JP | 200091096 | 3/2000 |
| WO | WO2004/104707 | 12/2004 |

OTHER PUBLICATIONS

Apruzese, "X-ray laser reearch using z pinches," Am. Inst. Of Phys. 399-403 (1994).
Bollanti et al., "Compact three electrodes excimer laser IANUS for a POPA optical system," SPIE Proc. (2206) 144-153 (1994).
Bollanti et al., "Ianus the three-electrode excimer laser," Appl. Phys. B (Lasers & Optics) 66(4):401-406, (1998).
Braun et al., "Multi-compound EUV multiplayer Mirrors," Proc. SPIE, 5037:2-13 (2003).
Choi et al., "A $10^{13}$ A/s high energy density micro discharge radiation source," B. Radiation Characteristics, p. 287-290.
Choi et al., "Fast pulsed hollow cathode capillary discharge device," Rev. of Sci. Instrum. 69(9):3118-3122 (1998).
Choi et al., "Temporal development of hard and soft x-ray emission from a gas-puff Z pinch," Rev. Sci. Instrum. 57(8), pp. 2162-2164 (Aug. 1986).
Coutts et al., "High average power blue generation from a copper vapour laser pumped titanium sapphire laser", Journal of Modern Optics, vol. 45, No. 6, p. 1185-1197 (1998).
Eichler et al., "Phase conjugation for realizing lasers with diffraction limited beam quality and high average power", Techninische Universitat Berlin, Optisches Institut, (Jun. 1998).
Fedosejevs and A. A Offenberger, "Subnanosecond pulses from a KrF laser pumped SF6 brillouin amplifier", IEEE J. QE 21, 1558-1562 (1985).
Feigl et al., "Heat resistance of EUV multiplayer mirrors for long-time applications," Microelectronic Engineering, 57-58:3-8 (2001).
Fomenkov et al., "Characterization of a 13.5 nm source for EUV lithography based on a dense plasma focus and lithium emission," Sematech Intl. Workshop on EUV Lithography (Oct. 1999).
Giordano et al., "Magnetic pulse compressor for prepulse discharge in spiker-sustainer excitati technique for XeCl lasers," Rev. Sci. Instrum 65(8), pp. 2475-2481 (Aug. 1994).
Hansson et al., "Xenon liguid jet laser-plasma source for EUV lithography," Emerging Lithographic Technologies IV, Proc. of SPIE, vol. 3997:729-732 (2000).
Hercher, "Tunable single mode operation of gas lasers using intracavity tilted etalons," Applied Optics, vol. 8, No. 6, Jun. 1969, pp. 1103-1106.
Jahn, Physics of Electric Propulsion, McGraw-Hill Book Company, (Series in Missile and Space U.S.A.) Chap. 9, "Unsteady Electromagnetic Acceleration," p. 257 (1968).
Jiang et al., "Compact multimode pumped erbium-doped phosphate fiber amplifiers," Optical Engineering, vol. 42, Issue 10, pp. 2817-2820 (Oct. 2003).
Kato, "Electrode Lifetimes in a plasma focus soft x-ray source," J. Appl. Phys. (33) Pt. 1, No. 8:4742-4744 (1991).
Kato et al., "Plasma focus x-ray source for lithography," Am. Vac. Sci. Tech. B. 6(1): 1950198 (1988).
Kuwahara et al., "Short-pulse generation by saturated KrF laser amplification of a steep stokes pulse produced by two-step stimulated brillouin scattering", J. Opt. Soc. Am. B 17, 1943-1947 (2000).
Lange et al., "High gain coefficient phosphate glass fiber amplifier," NFOEC 2003, paper No. 126.

Lebert et al., "Soft x-ray emission of laser-produced plasmas using a low-debris cryogenic nitrogen target," J. App. Phys., 84(6):3419-3421 (1998).
Lebert et al., "A gas discharged based radiation source for EUV-lithography," Intl. Conf. Micro and Nano-Engineering 98 (Sep. 22-24, 1998) Leuven, Belgium.
Lebert et al., "Investigation of pinch plasmas with plasma parameters promising ASE," Inst. Phys. Conf. Ser No. 125 Section 9, pp. 411-415 (1992) Schiersee, Germany.
Lebert et al., "Comparison of laser produced and gas discharge based EUV sources for different applications," Int. Conf. Micro-and Nano-Engineering 98 (Sep. 22-24, 1998) Leuven, Belgium.
Lee, "Production of dense plasmas in hypocycloidal pinch apparatus," The Phys. of Fluids, 20(2):313-321 (1977).
Lewis, "Status of collision-pumped x-ray lasers," Am. Inst. Phys. pp. 9-16 (1994).
Lowe, "Gas plasmas yield x-rays for lithography," Electronics, pp. 40-41 (Jan. 27, 1982).
Malmqvist et al., "Liquid-jet target for laser-plasma soft x-ray generation," Am. Inst. Phys. 67(12):4150-4153 (1996).
Mather, "Formation of a high-density deuterium plasma focus," The Physics of Fluids, 8(2), 366-377 (Feb. 1965).
Mather et al., "Stability of the dense plasma focus," Phys. of Fluids (12(11):2343-2347 (1969).
Matthews et al., "Plasma source for x-ray lithography," SPIE 333 Submicron Lithography, pp. 136-139 (1982).
Maruyama et al., Characteristics of high-power excimer laser master oscillator power amplifier system for dye laser pumping, Optics Communications, vol. 87, No. 3 p. 105-108 (1992).
Mayo et al., "A magnetized coaxial source facility for the generation of energetic plasma flows," Sci. Technol. vol. 4, pp. 47-55 (1994).
Mayo et al., "Initial results on high enthalpy plasma generation in a magnetized coaxial source," Fusion Tech vol. 26:1221-1225 (1994).
Nilsen et al., "Analysis of resonantly photopumped Na—Ne x-ray laser scheme," Am. Phys. Soc. 44(7):4591-4597 (1991).
Nishioka et al., "UV saturable absorber for short-pulse KrF laser systems", Opt. Lett. 14, 692-694 (1989).
Orme et al., "Electrostatic charging and deflection of nonconventional droplet streams formed from capillary stream breakup," Physics of Fluids, 12(9):2224-2235, (Sep. 2000).
Orme et al., "Charged molten droplet deposition as a direct write technology," MRS 2000 Spring Meeting, san Francisco, (Apr. 2000).
Pant et al., "Behavior of expanding laser produced plasma in a magnetic filed," Physica Scripta, T75:104-111, (1998).
Partlo et al., "EUV (13.5nm) light generation using a dense plasma focus device," SPIE Proc. on Emerging Lithographic Technologies III, vol. 3676, 846-858 (Mar. 1999).
Pearlman et al., "x-ray lithography using a pulsed plasma source," J. Vac. Sci. Technol., pp. 1190-1193 (Nov./Dec. 1981).
Porter et al., "Demonstration of population inversion by resonant photopumping in a neon gas cell irradiated by a sodium Z pinch," Phys. Rev. Let., 68(6): 796-799, (Feb. 1992).
Price, "X-ray microscopy using grazing incidence reflection optics," Am. Inst. Phys., pp. 189-199 (1981).
Qi et al., "Fluorescence in Mg IX emission at 48.340 Å from Mg pinch plasmas photopumped by Al XI line radiation at 48.338 Å," The Am. Phys. Soc., 47(3):2253-2263 (Mar. 1993).
Scheuer et al., "A magnetically-nozzled, quasi-steady, multimegawatt, coaxial plasma thruster," IEEE:Transactions on Plasma Science, 22(6) (Dec. 1994).
Schiemann et al., "Efficient temporal compression of coherent nanosecond pulses in a compact SBS generator amplifier setup", IEEE J. QE 33, 358-366 (1997).
Schriever et al., "Laser-produced lithium plasma as a narrow-band extended ultraviolet radiation source for photoelectron spectroscopy," App. Optics, 37(7):1243-1248, (Mar. 1998).
Schriever et al., "Narrowband laser produced extreme ultraviolet sources adapted to silicon/molybdenum multiplayer optics," J. of App. Phys., 83(9):4566-4571, (May 1998).
Shiloh et al., "Z pinch of a gas jet," Physical Review Lett., 40(8), pp. 515-518 (Feb. 20, 1978).

Silfvast et al., "High-power plasma discharge source at 13.5 nm and 11.4 nm for EUV lithography," SPIE, vol. 3676:272-275 (Mar. 1999).

Silfvast et al., "Lithium hydride capillary discharge creates x-ray plasma at 13.5 nanometers," Laser Focus World, p. 13 (Mar. 1997).

Stallings et al., "Imploding argon plasma experiments," Appl. Phys. Lett., 35(7), pp. 524-526 (Oct. 1, 1979).

Tada et al., "1-pm spectrally narrowed compact ArF excimer laser for microlithography", Laser and Electro-Optics, CLEO '96, CThG4, p. 374 (1996).

Takahashi et al., "KrF laser picosecond pulse source by stimulated scattering processes", Opt. Commun. 215, 163-167 (2003).

Takahashi et al., High-intensity short KrF Laser-pulse generation by saturated amplification of truncated leading-edge pulse, Opt. Commun. 185, 431-437 (2000).

Tillack et al., "Magnetic confinement of an expanding laser-produced plasma," UC San Diego, Center for Energy Research, UCSD Report & Abramova—Tornado Trap.

Wilhein et al., "A slit grating spectrograph for quantitative soft x-ray spectroscopy," Am. Ins.t of Phys. Rev. of Sci. Instrum., 70(3):1694-1699, (Mar. 1999).

Wu et al., "The vacuum spark and spherical pinch x-ray/EUV point sources," SPIE, Conf. on Emerging Tech. III, Santa Clara, CA vol. 3676:410-420, (Mar. 1999).

Yusheng et al., "Recent progress of "Heaven-One" high power KrF excimer laser system", Laser and Electro-Optics, CLEO '96, CThG4, p. 374 (1996).

Zombeck, "Astrophysical observations with high resolution x-ray telescope," Am. Inst. Of Phys. pp. 200-209, (1981).

SYSTEMS AND METHODS FOR CLEANING A CHAMBER WINDOW OF AN EUV LIGHT SOURCE

CROSS-REFERENCE TO RELATED APPLICATIONS

The present application is a continuation-in-part application of U.S. patent application Ser. No. 11/174,442, entitled SYSTEMS AND METHODS FOR REDUCING THE INFLUENCE OF PLASMA-GENERATED DEBRIS ON THE INTERNAL COMPONENTS OF AN EUV LIGHT SOURCE, filed on Jun. 29, 2005, which is a continuation-in-part application of U.S. patent application Ser. No. 10/979,945, entitled LPP EUV LIGHT SOURCE, filed on Nov. 1, 2004, the disclosures of each of which are hereby incorporated by reference herein.

The present application is also a continuation-in-part application of U.S. patent application Ser. No. 11/067,099, entitled SYSTEMS FOR PROTECTING COMPONENTS OF AN EUV LIGHT SOURCE FROM PLASMA-GENERATED DEBRIS, filed on Feb. 25, 2005, the disclosure of which is hereby incorporated by reference herein.

The present invention is also related to U.S. patent application Ser. No. 10/900,839, entitled EUV LIGHT SOURCE, filed on Jul. 27, 2004, U.S. patent application Ser. No. 10/803,526, entitled HIGH REPETITION RATE LPP EUV LIGHT SOURCE, filed on Mar. 17, 2004, and U.S. patent application Ser. No. 10/798,740, entitled COLLECTOR FOR EUV LIGHT, filed on Mar. 10, 2004, the disclosures of each of which are hereby incorporated by reference herein.

FIELD OF THE INVENTION

The present invention relates to extreme ultraviolet ("EUV") light generators providing EUV light from a plasma created from a source material and collected and directed to a focus for utilization outside of the EUV light source generation chamber, e.g., for semiconductor integrated circuit manufacturing photolithography e.g., at wavelengths of around 50 nm and below.

BACKGROUND OF THE INVENTION

Extreme ultraviolet ("EUV") light, e.g., electromagnetic radiation having wavelengths of around 50 nm or less (also sometimes referred to a soft x-rays), and including light at a wavelength of about 13.5 nm, can be used in photolithography processes to produce extremely small features in substrates, e.g., silicon wafers.

Methods to produce EUV light include, but are not necessarily limited to, converting a material into a plasma state that has an element, e.g., xenon, lithium or tin, with an emission line in the EUV range. In one such method, often termed electric discharge produced plasma ("DPP"), the plasma may be produced by an electrical discharge between a pair of electrodes. In another method, the required plasma can be produced by irradiating a target material, such as a droplet, stream or cluster of material having the required line-emitting element, with a laser beam. This later process is generally referred to as laser produced plasma ("LPP").

For each of these processes, the plasma is typically produced in a sealed vessel, e.g., vacuum chamber, and monitored using various types of metrology equipment. In addition to generating EUV radiation, these plasma processes also typically generate undesirable by-products in the plasma chamber which can include heat, high energy ions and scattered debris from the plasma formation, e.g., atoms and/or clumps/microdroplets of source material that is not fully ionized in the plasma formation process.

These plasma formation by-products can potentially damage or reduce the operational efficiency of the various plasma chamber optical elements including, but not limited to, collector mirrors including multi-layer mirrors (MLM's) capable of EUV reflection at normal incidence and grazing angle incident mirrors, the surfaces of metrology detectors, windows used to image the plasma formation process, and in the case of LPP, the laser input window. The heat, high energy ions and/or source material debris may be damaging to the optical elements in a number of ways, including heating them, coating them with materials which reduce light transmission, penetrating into them and, e.g., damaging structural integrity and/or optical properties, e.g., the ability of a mirror to reflect light at such short wavelengths, corroding or eroding them and/or diffusing into them. In addition, some optical elements, e.g., the laser input window, form a part of the vacuum chamber and are thus placed under a stress when a vacuum is present in the plasma chamber. For these elements, deposits and heat can combine to fracture (i.e., crack) the element resulting in a loss of vacuum and requiring a costly repair.

Accessing contaminated or damaged optical elements in the plasma chamber for the purpose of cleaning or replacing the elements can be expensive, labor intensive and time-consuming. In particular, these systems typically require a rather complicated and time consuming purging and vacuum pump-down of the plasma chamber prior to a re-start after the plasma chamber has been opened. This lengthy process can adversely affect production schedules and decrease the overall efficiency of light sources for which it is typically desirable to operate with little or no downtime.

With the above in mind, Applicants disclose systems and methods for cleaning a chamber window of an EUV light source.

SUMMARY OF THE INVENTION

A cleaning system for a chamber window of an extreme ultraviolet (EUV) light source is disclosed. The window may have an inside surface facing a chamber interior and an opposed outside surface and the light source may generate debris by plasma formation. For the system, a subsystem may be positioned outside the chamber and may be operable to heat debris accumulating on the inside surface of the window.

In a first embodiment, the subsystem may place a flowing, heated gas, e.g. argon, helium, nitrogen, air or a combination thereof, in contact with the outside surface of the window. In one implementation, the system may further include an enclosing wall that is positioned outside the chamber and has a first end which surrounds the window. The enclosing wall may establish a volume and be formed with an inlet to introduce the gas into the volume and an outlet to exhaust the gas from the volume. In a particular arrangement, a second window may be mounted in the enclosing wall and aligned to allow a laser beam to pass sequentially through the second window and through the chamber window to enter the chamber for the purpose of creating a laser-produced plasma (LPP).

In another embodiment, the energy passed through the window may be electromagnetic radiation. The subsystem may include one or more microwave radiation emitter(s)

which may, for example emit electromagnetic radiation having a wavelength in the range of about 1 mm to 3 cm.

In another aspect, the light source may use a plasma formation material and the cleaning system may include an etchant for the plasma formation material that is introduced into the chamber. With this arrangement, the subsystem may heat deposited plasma formation material on the inside surface of the window to a temperature greater than 150° C. to increase a rate of a chemical reaction between deposited plasma formation material and the etchant. In one application, the plasma formation material may be Sn and the etchant may be HBr, $Br_2$, $Cl_2$, HCl, $H_2$ or a combination thereof.

The cleaning system may be used to clean a laser input window and may include a conical shroud that is positioned in the chamber, the shroud having a first end surrounding the window and a second open end. A system for flowing a gaseous etchant in the shroud may be provided. The window may, for example, be made of fused silica, ZnSe, NaCl, KCl or $CaF_2$.

In another aspect of an embodiment, a cleaning system for a chamber window of an EUV light source, wherein the light source utilizes a plasma formation material and generates debris by plasma formation, may include an etchant source to introduce an etchant for the plasma formation material into the chamber. The cleaning system may also include a heating subsystem directing heated gas toward the window to heat deposited plasma formation material on a surface of the window to a temperature greater than 150° C. to increase a rate of a chemical reaction between deposited plasma formation material and the etchant.

In still another aspect, a cleaning system for a chamber window of a laser produced plasma EUV light source, wherein the light source utilizes a plasma formation material and generates debris by plasma formation may include a conical shroud that is positioned in the chamber and has a first end surrounding the window and a second open end. An etchant source may be provided to introduce an etchant for the plasma formation material into the shroud. Also, a heating subsystem may be provided to direct microwave radiation toward the window to heat deposited plasma formation material on a surface of the window to a temperature greater than 150° C. to increase a rate of a chemical reaction between deposited plasma formation material and the etchant.

DETAILED DESCRIPTION OF PREFERRED EMBODIMENTS

Figure 1:
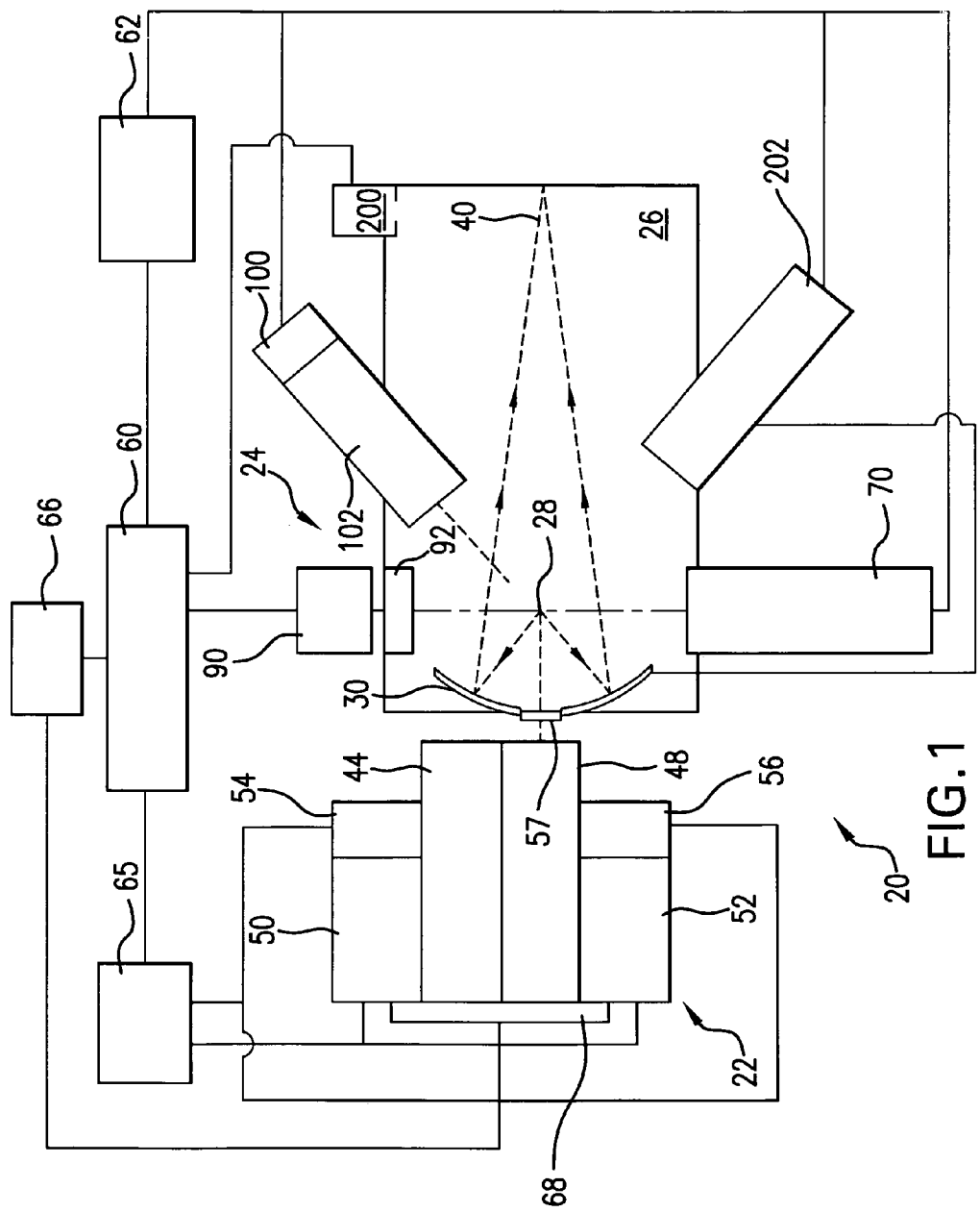
FIG. 1 shows a schematic view of an overall broad conception for a laser-produced plasma EUV light source according to an aspect of the present invention.

Turning now to FIG. 1 there is shown a schematic view of an exemplary production EUV light source, e.g., a laser produced plasma EUV light source 20 according to an aspect of the present invention. Although aspects of the present invention are illustrated with reference to a laser produced plasma (LPP), it is to be appreciated that certain aspects of the present invention may be equally applicable to other types of light sources which produce a plasma including an electric discharge produced plasma ("DPP"), a representative construction of which is disclosed in co-owned U.S. Pat. No. 6,815,700, which is hereby incorporated by reference.

Continuing with FIG. 1, an LPP light source 20 may contain a pulsed laser system 22, e.g., a gas discharge excimer or molecular fluorine laser operating at high power and high pulse repetition rate and may be a MOPA configured laser system, e.g., as shown in U.S. Pat. Nos. 6,625,191, 6,549,551, and 6,567,450. Depending on the application, other types of lasers may also be suitable. For example, a gas discharge laser such as $CO_2$ laser, a solid state laser, an excimer laser having a single chamber, an excimer laser having more than two chambers, e.g., an oscillator chamber and two amplifying chambers (with the amplifying chambers in parallel or in series), a master oscillator/power oscillator (MOPO) arrangement, a power oscillator/power amplifier (POPA) arrangement, or a solid state laser that seeds one or more excimer amplifier or oscillator chambers, may be suitable. Other designs are possible.

The light source 20 may also include a target delivery system 24, e.g., delivering targets in the form of liquid droplets, a liquid stream, solid particles or clusters, solid particles contained within liquid droplets or solid particles contained within a liquid stream. The targets may be delivered by the target delivery system 24, e.g., into the interior of a chamber 26 to a plasma formation site 28.

Laser pulses may be delivered from the pulsed laser system 22 along a laser optical axis through a laser input window 57 and into the chamber 26 to the irradiation site, suitably focused, to create a plasma, having certain characteristics which depend on the source material of the target. These characteristics may include the wavelength of the EUV light produced and the type and amount of debris released from the plasma.

The light source may also include a collector 30, e.g., a reflector, e.g., in the form of a truncated ellipse, with an aperture to allow the laser light to pass through and reach the ignition site 28. The collector 30 may be, e.g., an elliptical mirror that has a first focus at the ignition site 28 and a second focus at a so-called intermediate point 40 (also called the intermediate focus 40) where the EUV light is output from the light source and input to, e.g., an integrated circuit lithography tool (not shown).

The pulsed system 22 may include a dual chamber, e.g., a master oscillator-power amplifier ("MOPA"), gas discharge laser system having, e.g., an oscillator laser system 44 and an amplifier laser system 48, with, e.g., a magnetic reactor-switched pulse compression and timing circuit 50 for the oscillator laser system 44 and a magnetic reactor-switched pulse compression and timing circuit 52 for the amplifier laser system 48, along with a pulse power timing monitoring system 54 for the oscillator laser system 44 and a pulse power timing monitoring system 56 for the amplifier laser system 48. The system 20 may also include an EUV light source controller system 60, which may also include, e.g., a target position detection feedback system 62 and a firing control system 65, along with, e.g., a laser beam positioning system 66.

The system 20 may also include a target position detection system which may include one or more droplet imagers 70 that provide an output indicative of the position of a target droplet, e.g., relative to the ignition site and provide this output to the target position detection feedback system, which can, e.g., compute a target position and trajectory, from which a target error can be computed, if not on a droplet by droplet basis then on average. The target error may then be provided as an input to the system controller 60, which can, e.g., provide a laser position, direction and timing correction signal, e.g., to the laser beam positioning system 66 that the laser beam positioning system can use, e.g., to control the laser timing circuit and/or to control the laser position and direction changer 68, e.g., to change the focus point of the laser beam to a different ignition point 28.

The target delivery control system 90, in response to a signal from the system controller 60 may, e.g., modify the release point of the target droplets as released by the target delivery mechanism 92 to correct for errors in the target droplets arriving at the desired ignition site 28. An EUV light source detector 100 may also provide feedback to the system controller 60 that can be, e.g., indicative of the errors in such things as the timing and focus of the laser pulses to properly intercept the target droplets in the right place and time for effective and efficient EUV light production.

As shown schematically in FIG. 1 and described in more detail below, an aspect of an embodiment of the present invention can include a shielding system 102 for protecting a surface of a plasma chamber optical element from debris generated at the plasma formation site 28. Although the shielding system 102 is shown positioned to protect a surface of an EUV light source detector 100, it is to be appreciated that the shielding system 102 can be used to protect other optical elements in the chamber 26.

Figure 2:
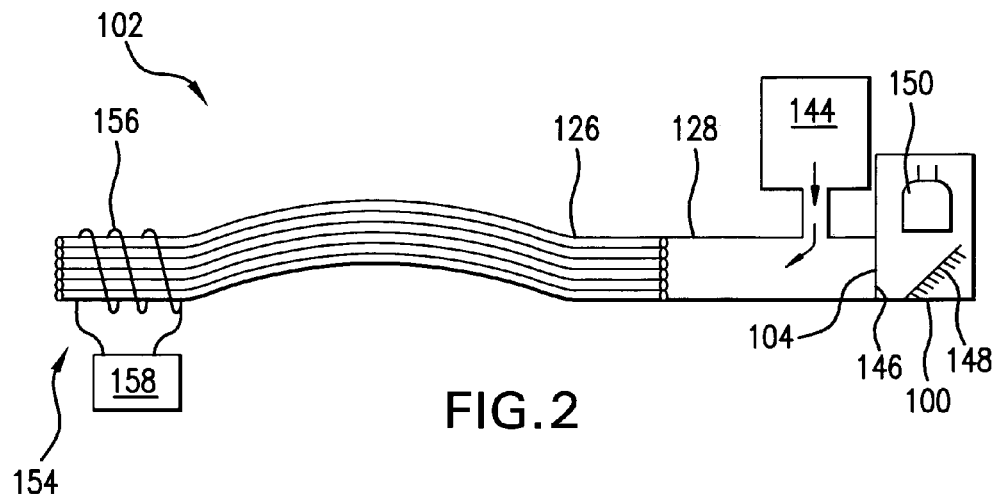
FIG. 2 shows a schematic, side view of an aspect of an embodiment of a shield system for protecting a plasma chamber optical element from plasma source material debris.
Figure 3:
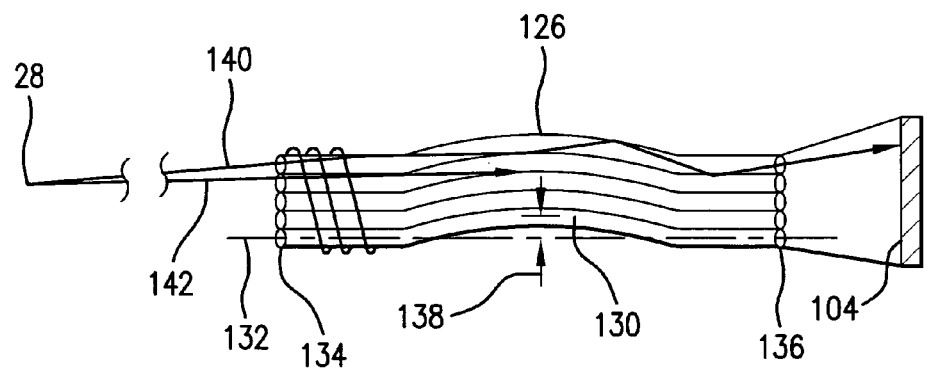
FIG. 3 shows a schematic, side view of a plurality of hollow tubes illustrating the path of an exemplary light ray through a hollow tube and the path of an exemplary debris particle being captured by a hollow tube.

FIG. 2 shows in more detail a system 102, for protecting a surface 104 of an optical element, e.g., EUV light detector 100, from plasma generated debris. As shown, the system 102 may include a plurality of hollow tubes 126, e.g., so-called capillary tubes, with each tube having a tube wall that surrounds a tube lumen (i.e., bore). Tubes 126 may be made of a material, e.g., glass, metal or ceramic, e.g., borosilicate material, which reflects EUV light at grazing angles of incidence, e.g., grazing incidence reflection at small (<10 degrees) angles of grazing incidence where the EUV reflectivity of smooth surfaces is relatively high for most materials. As shown, the tubes 126 may be grouped together and housed within a stainless steel housing tube 128 having a similar shape as the tubes 126. In an exemplary embodiment, about 50 bent glass capillary tubes 126, (1 mm outer diameter, 0.78 mm inner diameter, 150 mm long) may be mounted inside of a bent stainless steel tube 128. As shown in FIG. 3, the tubes 126 may be shaped having a midsection 130 that may be laterally offset from a tube axis 132 defined by the tube ends 134, 136. In particular, the midsection 130 may be offset by a distance 138 that is larger than inner diameter of the tube 126.

FIG. 3 shows that the tubes 126 may be interposed between the plasma formation site 28 and the detector surface 104. FIG. 3 also shows an exemplary path 140 of an EUV light ray and the exemplary path 142 of a debris particle. As shown, the EUV light ray passes through the lumen (i.e., bore) of a tube 126 after one or more small angle grazing incidence reflections from the inner wall surface of the tube 126 and reaches the surface 104. On the other hand, as shown, the debris particle may strike the inner wall of the hollow tube and stick to the inner wall. Moreover, in some cases, the accumulation of debris on the inner wall may result in a surface that may be smooth enough to adequately reflect EUV light at grazing angles of incidence. Use of the tubes 126 may have an advantage over the use of flat mirrors to direct light to a detector in that they will direct the light towards the end of the tube and no complicated alignment is required, like in the case of redirecting mirrors.

In use, the tubes 126 may be positioned inside the plasma chamber 26 (see FIG. 1) and located between the plasma formation site 28 and an optical element, e.g., detector 100, to thereby allow debris to temporarily deposit on the inner wall surfaces of the tubes 126. As shown, detector 100 may include one or more thin EUV filter foils 146, a multi-layer mirror 148 and a photodiode detector 150.

Continuing with FIG. 2, the system 102 may include a heater 154 to heat a portion of each tube 126, or in some cases each tube may be heated in its entirety, to a temperature sufficient to remove at least a portion of the deposited debris, e.g., to remove portions (or all) of one or more deposited species. The application of heat may also function to smooth out deposits and thereby increase grazing angle reflections. For example, the heater may heat the tubes 126 to a temperature sufficient to vaporize at least a portion of a deposited material. For a plasma source material which comprises Li, the heater 154 may be designed to heat the shield 108' to a temperature in the range of about 400 to 550° C. to vaporize Li from the tube surface.

In some cases, the heater may heat the tubes 126 to a temperature sufficient to initiate, and/or substantially increase the rate of, a chemical reaction between a deposited material and an etchant gas that is introduced into the tubes 126. FIG. 2 shows that the system 102 may include a sub-system 144 for releasing an etchant for flow into each tube 126. As shown, the sub-system 144 may be positioned to release etchant for travel through the tubes 126 from the detector 100 and toward the chamber 26. Suitable etchants can include, but are not necessarily limited to etchants such as $HBr$, $Br_2$, $Cl_2$, $HCl$, $H_2$, $HCF_3$ and combinations thereof. For example, an HBr concentration of a few Torr can be used.

For a plasma source material which comprises Sn, the heater 154 may be designed to heat the tubes 126 (or portions thereof) to a temperature in the range of about 150 to 400° C., and for some applications greater than 300° C., to initiate a reaction between Sn deposits and one or more gaseous etchants, e.g., HBr, to create a reaction product that may be removed from the inner tube wall.

In more structural detail, as shown in FIG. 2, the heater 154 may comprise a heating element 156 that is wrapped around the tubes 126, and a current source 158 for passing a current through the heating element 156. The heating element 156 may be made of a conductive material, and thus be heated via ohmic heating during current flow. Other means of heating the tubes 126 may include, but are not limited to radiative heaters, microwave heaters, RF heaters and combinations thereof.

Figure 4:
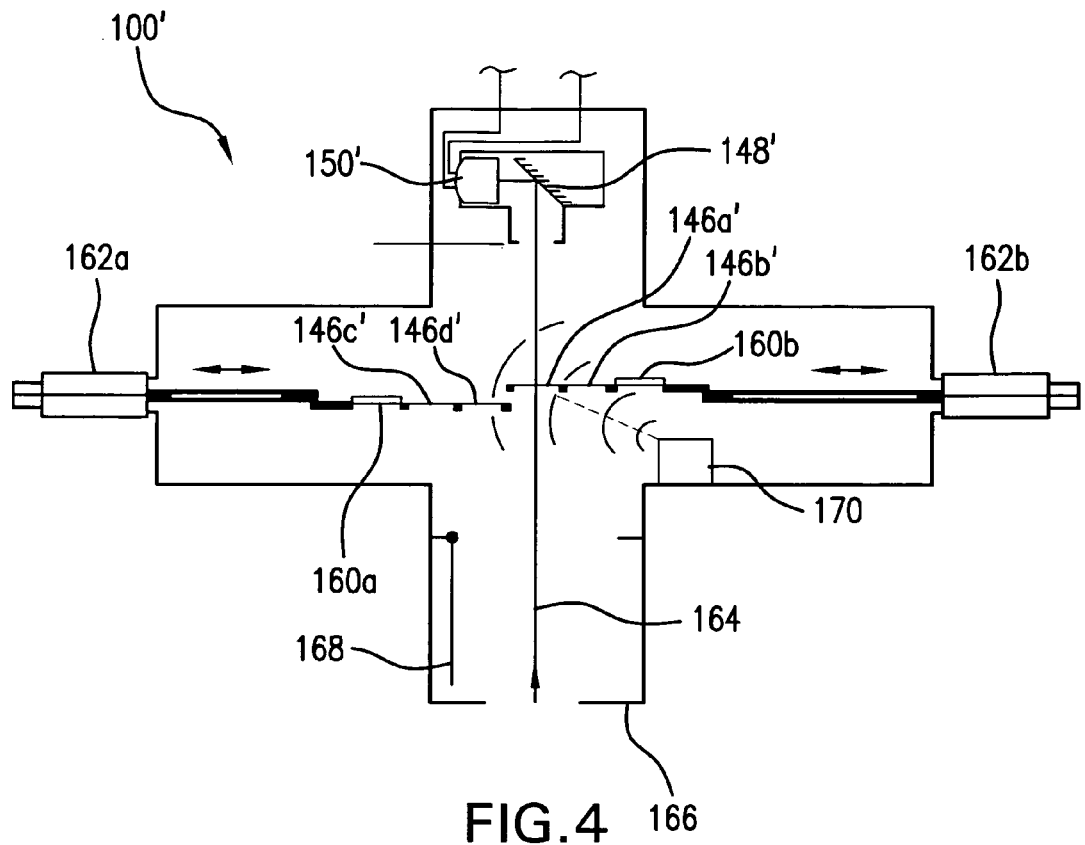
FIG. 4 shows a schematic, sectional view of an aspect of an embodiment of the present invention wherein an EUV metrology monitor may comprise a heater to heat a filter foil to remove deposited plasma generated debris.

FIG. 4 shows another aspect of an embodiment of the present invention which may comprise an EUV metrology monitor 100' having a detector 150' for measuring EUV light parameters, e.g., pulse energy or flux. In some applications, it may be desirable for the detector to measure light having a wavelength of about 13.5 nm and a bandwidth of about 2% or less. For this purpose, light from the EUV light source may be filtered at the monitor 100'. Specifically, as shown, the monitor 100' may comprise one or more filter foils 146a', 146b', 146c' and 146d', one or more $CaF_2$ windows 160a,b, and one or more multi-layer mirrors 148' capable of reflecting a band of light centered on 13.5 nm at normal incidence. It is to be appreciated that the multi-layer mirrors 148', e.g., multilayer mirrors having alternating layers of $MoSi_2$ and Si, may absorb light, e.g., light outside the 2% band centered on 13.5 nm, and thus, may act as a band-pass optical filter. On the other hand, when a $CaF_2$ window 160a,b is interposed along the beam path, EUV light may be absorbed while UV and visible light may be transmitted through the window 160a,b. Thus, the $CaF_2$ window 160a,b may also act as an optical filter. Similarly, the filter foils 146a'-d', which may be comprised of a thin layer of antimony, may absorb or reflect visible light while transmitting EUV radiation.

FIG. 2 further shows that the monitor 100' may include a pair of linear motion actuators 162a,b to selectively interpose one or more filters 146a'-d', 160a,b along the beam path 164. The monitor 100' may also include an entrance aperture 166 and fast shutter 168. With this arrangement, the filters 146a'-d', 160a,b may be undesirable exposed to plasma generate debris entering the monitor 100' through the entrance aperture 166. In some cases, debris deposits may reduce the operational efficiency of the filters 146a'-d', 160a,b. With this in mind, the monitor 100' may include a heater 170, which for the monitor 100' that is shown can be a radiative heater, to heat a filter 146a'-d', 160a,b to remove plasma generated debris that has temporarily deposited thereon. Other means of heating the filters 146a'-d', 160a,b may include, but are not limited to ohmic heaters, radiative heaters, microwave heaters, RF heaters and combinations thereof.

For a plasma source material which comprises Li, the heater 170 may be designed to heat the filter(s) 146a'-d', 160a,b to a temperature in the range of about 400 to 550° C. to vaporize Li from the filter surface. For a plasma source material which comprises Sn, the heater 170 may be designed to heat the filter(s) 146a'-d', 160a,b to a temperature in the range of about 150 to 400° C., and for some applications greater than 300° C., to initiate a reaction between Sn deposits and gaseous etchants, e.g., HBr, to create a reaction product that may be removed from the filter surface. Gaseous etchants can be introduced directly into the monitor 100' or into the chamber 26 (See FIG. 1).

Figure 5:
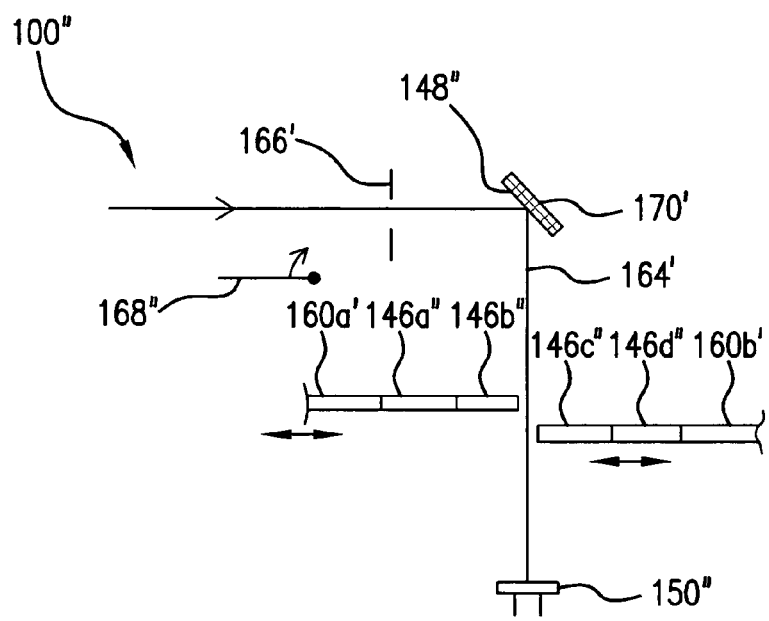
FIG. 5 shows a schematic, sectional view of another aspect of an embodiment of the present invention wherein an EUV metrology monitor may comprise a heater to heat a multi-layer mirror to remove deposited plasma generated debris.

FIG. 5 shows an alternative arrangement for a monitor (generally designated monitor 100"). As shown, the EUV metrology monitor 100" may have a detector 150" for measuring EUV light parameters, e.g., pulse energy or flux and may include one or more filters 146a", 146b", 146c" and 146d", 160a',b', one or more of which can be selectively interposed along beam path 164'. The monitor 100" may also include one or more multi-layer mirrors 148". It can be further seen that the monitor 100" may also include an aperture 166' and fast shutter 168'. With this arrangement, the multi-layer mirror 148" may be undesirable exposed to plasma generate debris entering the monitor 100" through the aperture 166'. Debris deposits may, in some cases, reduce the operational efficiency of the mirror 148". With this in mind, the monitor 100" may include a heater 170', which for the monitor 100' that is shown can be an ohmic heater that is mounted on the backside of the mirror 148", to heat the mirror 148" and remove plasma generated debris that has temporarily deposited thereon. Other means of heating the mirror 148" may include, but are not limited to radiative heaters, microwave heaters, RF heaters and combinations thereof.

For a plasma source material which comprises Li, the heater 170' may be designed to heat the mirror 148" to a temperature in the range of about 400 to 550° C. to vaporize Li from the mirror surface. For a plasma source material which comprises Sn, the heater 170 may be designed to heat the mirror 148" to a temperature in the range of about 150 to 400° C., and for some applications greater than 300° C., to initiate a reaction between Sn deposits and gaseous etchants, e.g., HBr, to create a reaction product that may be removed from the mirror surface. Gaseous etchants can be introduced directly into the monitor 100' or into the chamber 26 (See FIG. 1).

In one aspect of an embodiment of the present invention, as illustrated by FIG. 1, a target material containing Lithium may be used to generate a plasma at the plasma formation site 28. With this arrangement, debris containing Lithium and Lithium compounds may deposit on the collector mirror 30. Inherently, Lithium is very reactive material and reacts with almost any contaminant on a collector surface, and thus, creates lithium compounds. Typically, uncombined Lithium can be evaporated by heating the collector mirror 30 to an elevated temperature, e.g., 350-450° C. In particular, the temperature may be chosen to ensure that the Lithium evaporation rate is higher than the rate of lithium debris deposition. Unfortunately, some Lithium compounds do not evaporate at these moderate temperatures (i.e., 350-450° C.). For example, compounds such as $Li_2O$ or $Li_2CO_3$ required higher temperatures to evaporate and do not easily sputter from the surface of the collector 30. To evaporate lithium compounds may require the collector to be heated to very high temperature (above 600-700° C.) which may reduce or destroy the reflectivity of a typical multi-layer mirror. Thus, evaporation and or sputtering of lithium compounds may be problematic.

With the above in mind, FIG. 1 illustrates that a hydrogen source 150, e.g., a source of molecular or atomic hydrogen, e.g., atomic hydrogen from a remote plasma source, may be provided to introduce hydrogen into the chamber 26 for reaction with Lithium to create LiH. A sputtering system 202 may be provided to generate sputtering ions and/or molecules and direct them to the surface of the collector with sufficient energy to sputter LiH. For example, the sputtering system may establish an RF cleaning plasma, e.g., capacitive or inductively coupled, with helium or argon as the sputtering material. As shown, the collector 30 may be RF biased to selectively control the energy of ions bombarding debris that has deposited on the collector 30. It general, it can be significantly easier to sputter LiH from the collector surface than $Li_2O$ or $Li_2CO_3$. Also LiH deposits may be more transparent than $Li_2O$. Sputtering in this manner may be used alone to sputter Lithium and Lithium compounds or in combination with heat to evaporate Lithium and/or plasma etching.

Figure 6:
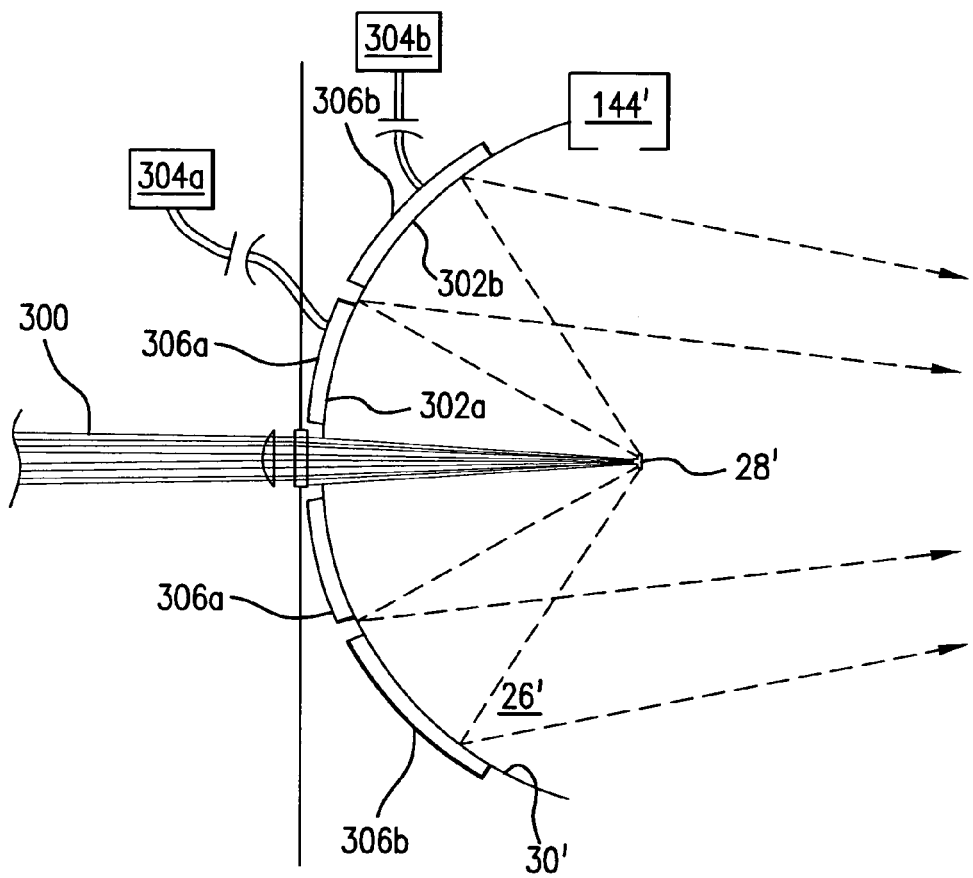
FIG. 6 illustrates an aspect of an embodiment of the present invention in which different zones of a collector mirror are etched to remove plasma generated debris at different etch rates.

FIG. 6 illustrates an aspect of an embodiment of the present invention in which a laser 300 is focused to a plasma formation site 28' in a chamber 26'. A collector 30', e.g., an elliptical collector having a first focal point at or near the plasma formation site and a second focal point at an intermediary focus (See FIG. 1) may be provided. With this arrangement, plasma generated debris may deposit at different rates at different zones on the collector mirror 30'. For example, more debris may deposit at location 302a than location 302b (note, for an elliptical collector, location 302b is farther from the plasma initiation site 28' than location 302a). Thus, for the system shown in FIG. 6 which uses plasma etching to remove debris from the collector 30', a higher etch rate may be desirable at location 302a than location 302b. (Note: it may be damaging to the mirror to continue etching a portion of the mirror after deposited debris has been removed). To this end, the system may include a source 144' of plasma etchant and first and second, independently controllable, RF power supplies 304a,b that are attached respectively through capacitors to separate RF electrodes 306a,b, as shown. Although two RF systems are shown for respectively operating on substantially annularly shaped collector zones, it is to be appreciated that more than two RF systems may be employed and the use of RF systems is not limited to zones having any specific shape, such as the annular shape shown.

Suitable etchants may include, but are not necessarily limited to etchants such as $HBr$, $Br_2$, $Cl_2$, $HCl$, $H_2$, $HCF_3$ and combinations thereof. A non-etching gas, e.g., Argon or Helium, may be introduced to establish the etching plasma. As used herein, the term "plasma etching" means a process which may include one or more of the following process steps: 1) generation of reactive species in a plasma; 2) diffusion of these species to the surface of the material being etched; 3) adsorption of these species on the surface; 4) occurrence of one or more chemical reactions between the species and the material being etched, forming volatile byproducts; 5) desorption of the byproducts from the surface; and 6) diffusion of the desorbed byproducts into the bulk of the gas. The embodiment shown in FIG. 6 can be used for target material containing Lithium, Tin, Xenon and/or other materials.

Figure 7:
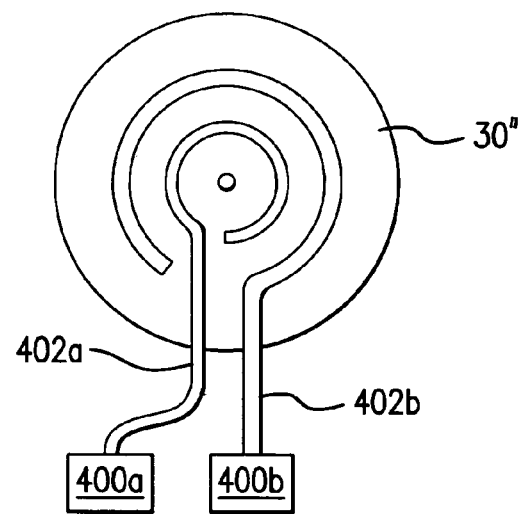
FIG. 7 illustrates another aspect of an embodiment of the present invention in which different zones of a collector mirror may be heated at different rates to remove plasma generated debris at different removal rates.

FIG. 7 illustrates another aspect of an embodiment of the present invention in which different zones of a collector 30'' may be heated at different rates. Specifically, an etch rate may be strongly dependent on temperature. For example, the rate of Tin removal using $HBr$ and/or $Br_2$ has been found to be strongly dependent on temperature in the range of 150-400° C. As shown in FIG. 7, which shows the backside of an exemplary elliptical collector 30'', differential heating may be employed using ohmic heating systems to establish different etch rates for different collector zones. Specifically, each heating system includes an electrical power source 400a,b connected to a respective, shaped conductor 402a,b. Other types of heaters for heating collector zones to differing temperatures may include, but are not limited to radiative heaters, microwave heaters, RF heaters and combinations thereof. The embodiment shown in FIG. 7 can be used for target material containing Lithium, Tin, Xenon and/or other materials.

Figure 8:
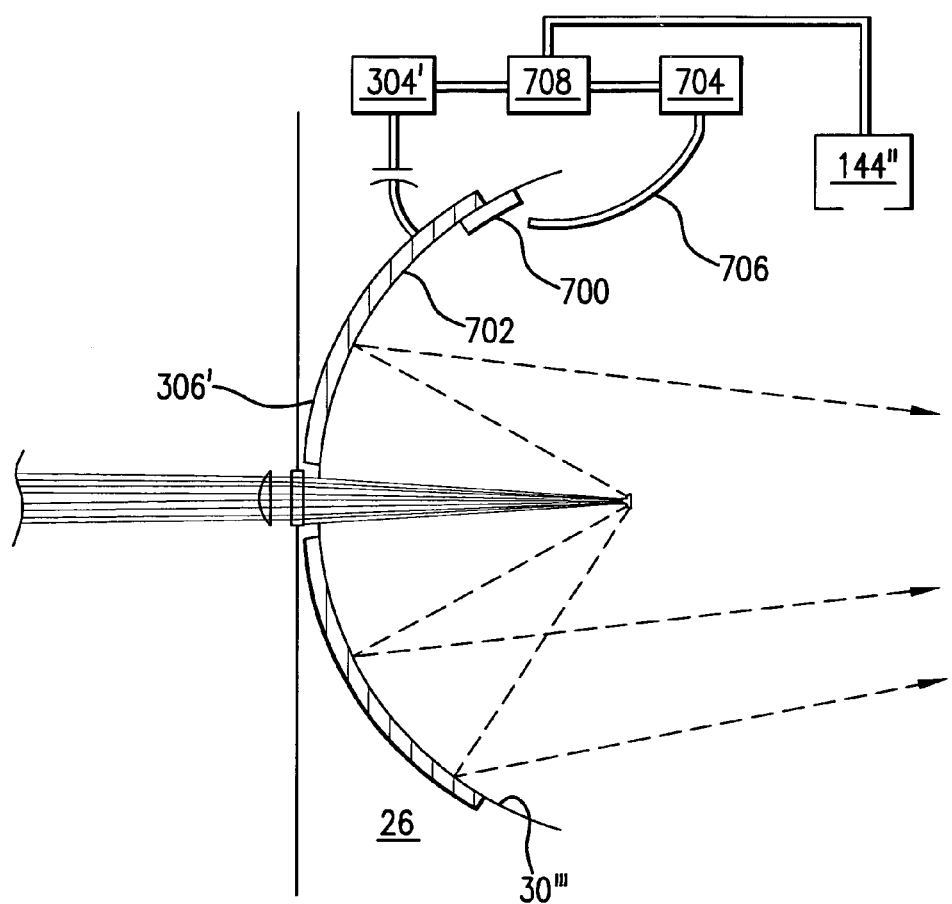
FIG. 8 illustrates another aspect of an embodiment of the present invention in which an apparatus for etching debris from a surface of a EUV light source collector mirror with a controlled plasma etch rate may be provided.

FIG. 8 illustrates another aspect of an embodiment of the present invention in which an apparatus for etching debris from a surface of a EUV light source collector mirror 30''' with a controlled plasma etch rate may be provided. As shown, the apparatus may include a reference material, e.g., witness plate 700, having a surface positioned to receive a substantially same amount of debris accumulation as location 702 on the surface of collector 30'''. For example, a small (about 1×1 cm) sacrificial witness plate 700 may placed next to the MLM collector 30''' and made of a material having a moderate halogen etch rate, such as In or Sb. With this arrangement, a plasma etch system can be deployed to etch debris from the plate 700 and location 702 on the collector 30''', at approximately the same etch rate. As shown, the plasma etch system can include a source 144'' of plasma etchant and a controllable, RF power supply 304' that is attached through a capacitor to RF electrode 306', as shown.

The system may further include an instrument 704 for analyzing etching plasma emission from the witness plate 700. For example, the instrument 704 may be a spectrometer. As shown, an optical fiber 706, e.g., fiber optic cable can be used to transmit etching plasma emission from the witness plate 700 to the instrument 704. Other suitable techniques for efficiently transmitted the etching plasma emission from the witness plate 700 to the instrument may include a focusing optic, e.g., lens (not shown). For the etch control system, the instrument may produce an output indicative of a debris accumulation amount on the witness plate 700. This output may then be received by a controller 708 which then used the output to vary an etch rate parameter to control plasma etch rate. For example, the controller 708 can vary the RF power or the etchant concentration in the chamber 26.

To measure the amount of debris accumulation on the witness plate 700, the instrument may measure a spectral line intensity for the witness plate material, e.g., In or Sb. If the witness material line intensity exceeds the highest allowable preselected value, the indication is that the etching efficiency exceeds the debris flux, e.g., Sn flux. In this case, the RF power or etchant concentration may be reduced by the controller 708. Alternatively, if the witness material line intensity becomes smaller than the specified minimum value, the indication is that the cleaning power of the etcher is insufficient for the arriving debris flux, e.g., Sn flux, and the RF power or etchant concentration may be increased.

The witness plate material spectral line intensity may be used as feedback to control RF power and/or etchant concentration to keep the witness plate material spectral line intensity (as measured by the instrument 704) at a specified level or within a specified range. Alternatively, a ratio of spectral intensities for the EUV plasma target, e.g., Tin, line and the witness material line can be kept at the specified target value or within a specified range.

Figure 9:
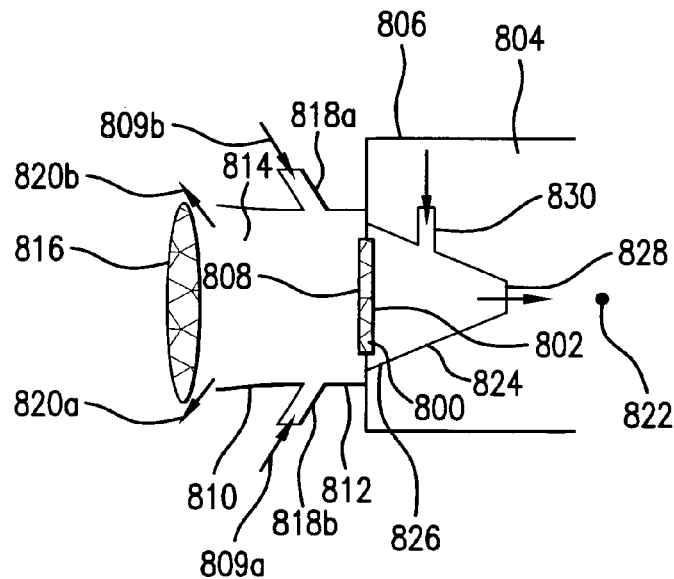
FIG. 9 shows a schematic, sectional view of an aspect of an embodiment of the present invention wherein a heated gas is used in cleaning a laser chamber window.

FIG. 9 shows another aspect of an embodiment in which a cleaning system for a chamber window 800 of an extreme ultraviolet (EUV) light source is illustrated. As shown, the window 800 may have an inside window surface 802 facing an interior 804 of a chamber 806 and an opposed outside window surface 808. For the light source shown, debris may be generated by plasma formation which may reach and contaminate the inside surface 802 of the window 800. For the cleaning system, an energy source, which for the case illustrated in FIG. 9 includes heated gas (represented by arrows 809a,b), may be positioned outside the chamber 806 and may be operable to uniformly heat the outside surface 808 of the window 800, and, via thermal conduction through the window 800, uniformly heat the inside surface 802 of the window 800 to heat debris accumulating on the inside surface 802.

For the embodiment shown, an enclosing wall 810 is positioned outside the chamber 806 and has a first end 812 which surrounds the window 800. With this structure, the enclosing wall 810 establishes a volume 814 between the window 800 and an LPP focusing lens 816. As shown, the enclosing wall 810 is formed with inlets 818a,b to introduce the gas 809a,b into the volume 814 and toward the outside window surface 808. Also shown, outlets 820a,b may be provided to exhaust the gas from the volume 814. In one setup, heated gas 21, which may be, for example Ar, He, $N_2$, air or combination thereof, at a pressure of about 10-20 torr above atmospheric pressure is blown through the inlets 818a,b and forced into contact with the laser window 800, thereby increasing its temperature. The circuitous path for the heated gas provided by the enclosing wall 810 increases contact between the gas and the window 800 and allows the gas to spend more time in the region of the window 800 to ensure a heat transfer that is efficient and uniform.

Continuing with FIG. 9, it can be seen that the light source established a plasma formation site 822 where a plasma formation material, such as tin, lithium or xenon is used to form a plasma and emit EUV radiation. With this arrangement, debris may be generated at the plasma formation site 822 which may contaminate the surface 802 of the window 800. An etchant capable of reaction with the plasma formation material may be introduced into the chamber 806 to clean the surface 802. In one application, the plasma formation material may be Sn and the etchant may be HBr, $Br_2$, $Cl_2$, HCl, $H_2$ or a combination thereof. With this arrangement, the heated gas 809a,b may heat deposited plasma formation material on the inside surface 802 of the window 800 to a temperature in the range of 150 to 400° C., and for some applications greater than 300° C., to increase a rate of a chemical reaction between deposited plasma formation material and the etchant.

FIG. 9 also shows that the cleaning system may include a conical shroud 824 (i.e. a so-called gas cone) that is positioned in the chamber 806, the shroud 824 having a first end 826 surrounding the window 800 and a second open end 828 to allow a laser beam to reach the plasma formation site 822. FIG. 9 shows that a gaseous etchant may be introduced into the shroud 824 via inlet 830 and flow out the shroud through the open end 828. Thus, flow is toward to plasma formation site 822, as shown.

In a typical LPP setup, it may be desirable to maintain a relatively strong vacuum in the chamber 806, and thus, the amount of etchant introduced into the chamber 806 is limited. As a consequence, the allowable etchant flow rate and pressure are generally too small to effectively heat the window 800 to a temperature sufficient to achieve a reasonable reaction rate between the etchant and debris deposits. For example, HBr gas at 600 degrees C. and at a pressure of 1 to 2 torr in the gas cone can only transport about 1 Watt of heating power at typical flow rates. On the other hand, when applying a heated gas to the outside surface 808, an elevated (greater than 1 atm) pressure can be used allowing the mass flow to be significantly higher and a power in the range of about $10^1$-$10^2$ W is feasible.

Figure 10:
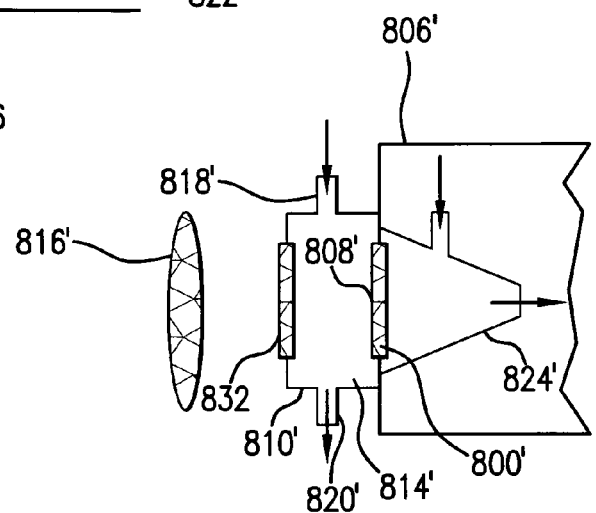
FIG. 10 shows a schematic, sectional view of an aspect of an embodiment of the present invention wherein an auxiliary chamber is provided to facilitate contacting a laser chamber window with a heated gas.

FIG. 10 shows another arrangement in which a second window 832 is mounted in the enclosing wall 810' and aligned to allow a laser beam to pass, sequentially, through the laser focusing lens 816', through the second window 832 and then through the chamber window 800' to enter the chamber 806' for the purpose of creating a laser-produced plasma (LPP). With this structure, a substantially closed auxiliary chamber is established allowing a heated gas, e.g. Ar, He, $N_2$, air or a combination thereof, to be introduced through inlet 818' into the volume 814' for contact with the outside surface 808' of the window 800'. Also shown, outlet 820' may be provided to exhaust the gas from the volume 814'. FIG. 10 also shows that this embodiment include a conical shroud 824' that is positioned in the chamber 806'. It is to be appreciated that a gaseous etchant may be introduced into the shroud 824' as described above.

Figure 11:
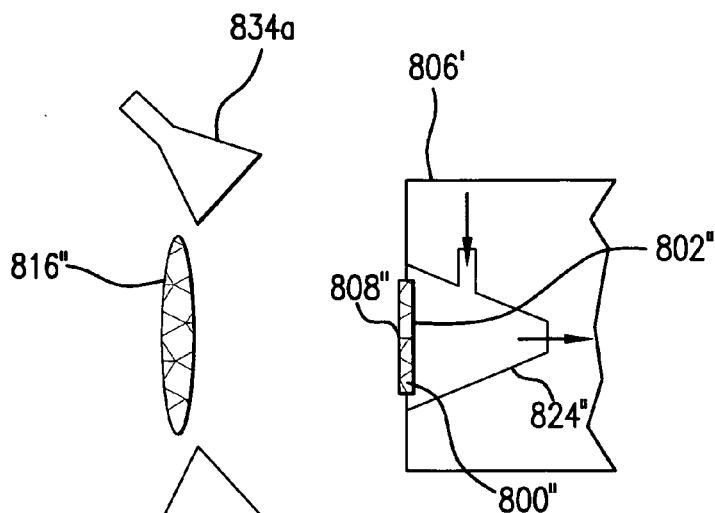
FIG. 11 shows a schematic, sectional view of an aspect of an embodiment of the present invention wherein microwave emitters located external to a chamber are used to heat a chamber window for the purpose of cleaning the window.

FIG. 11 shows another aspect of an embodiment of the present invention wherein microwave emitters 834a,b are located external to the chamber 806' and may be used to uniformly heat a chamber window 800' for the purpose of cleaning the window 800'. FIG. 11 also shows that this embodiment includes a conical shroud 824" that is positioned in the chamber 806". It is to be appreciated that a gaseous etchant may be introduced into the shroud 824" as described above. With this arrangement, microwave radiation may be directed through the window to heat plasma formation material, e.g. Sn, that has deposited on the inside surface 802" of the window 800" to a temperature in a range of 150 to 400° C., and for some applications greater than 300° C., to increase a rate of a chemical reaction between deposited plasma formation material and the etchant.

For the embodiment shown, one or more microwave radiators 834 may be uniformly distributed around the LPP laser focusing lens 816" and oriented to direct microwave radiation toward and through the laser input window 800". For example, a microwave wavelength of about 1 mm to 3 cm may be used with the total power of the radiators in a range of few the hundred watts to provide the required uniform temperature on the surface. The microwave radiation may be transmitted by the material of input window (fused silica, ZnSe, NaCl, KCl or $CaF_2$) and will be absorbed by a debris film, e.g. conducting Sn that has deposited on the inside surface 802" of the window 800". With this arrangement, a "self-controlled" mechanism of etching with temperature-controlled feedback may be achieved. Specifically, regions of the window 800" with highest Sn deposition (in area or thickness) will result in increased power absorption, and thus, increased etching rate, as compare to the other regions. Alternatively, laser sources such as CO or $CO_2$, producing non-focused laser radiation (e.g. one or more laser sources in addition to the LPP drive laser) may be used in place of the microwave emitters to pass radiation through the window for absorption by the debris.

It will be understood by those skilled in the art that the aspects of embodiments of the present invention disclosed above are intended to be preferred embodiments only and not to limit the disclosure of the present invention(s) in any way and particularly not to a specific preferred embodiment alone. Many changes and modification can be made to the disclosed aspects of embodiments of the disclosed invention (s) that will be understood and appreciated by those skilled in the art. The appended claims are intended in scope and meaning to cover not only the disclosed aspects of embodiments of the present invention(s) but also such equivalents and other modifications and changes that would be apparent to those skilled in the art. While the particular aspects of embodiment(s) described and illustrated in this patent application in the detail required to satisfy 35 U.S.C. §112 are fully capable of attaining any above-described purposes for, problems to be solved by or any other reasons for or objects of the aspects of an embodiment(s) above described, it is to be understood by those skilled in the art that it is the presently described aspects of the described embodiment(s) of the present invention are merely exemplary, illustrative and representative of the subject matter which is broadly contemplated by the present invention. The scope of the presently described and claimed aspects of embodiments fully encompasses other embodiments which may now be or may become obvious to those skilled in the art based on the teachings of the Specification. The scope of the present invention is solely and completely limited by only the appended claims and nothing beyond the recitations of the appended claims. Reference to an element in such claims in the singular is not intended to mean nor shall it mean in interpreting such claim element "one and only one" unless explicitly so stated, but rather "one or more". All structural and functional equivalents to any of the elements of the above-described aspects of an embodiment(s) that are known or later come to be known to those of ordinary skill in the art are expressly incorporated herein by reference and are intended to be encompassed by the present claims. Any term used in the specification and/or in the claims and expressly given a meaning in the Specification and/or claims in the present application shall have that meaning, regardless of any dictionary or other commonly used meaning for such a term. It is not intended or necessary for a device or method discussed in the Specification as any aspect of an embodiment to address each and every problem sought to be solved by the aspects of embodiments disclosed in this application, for it to be encompassed by the present claims. No element, component, or method step in the present disclosure is intended to be dedicated to the public regardless of whether the element, component, or method step is explicitly recited in the claims. No claim element in the appended claims is to be construed under the provisions of 35 U.S.C. §112, sixth paragraph, unless the element is expressly recited using the phrase "means for" or, in the case of a method claim, the element is recited as a "step" instead of an "act".

We claim:

1. A cleaning system for a chamber window of an EUV light source, said window having an inside surface facing a chamber interior and an opposed outside surface, said source generating debris by plasma formation, said system comprising;
   a subsystem positioned outside said chamber and operable to pass non-laser energy through said window to heat debris accumulating on said inside surface of said window.

2. A cleaning system as recited in claim 1 wherein said energy is heat.

3. A cleaning system as recited in claim 2 wherein said subsystem comprises a flowing, heated gas in contact with said outside surface of said window.

4. A cleaning system as recited in claim 3 wherein said gas is selected from the group of gases consisting of argon, helium, nitrogen, air and combinations thereof.

5. A cleaning system as recited in claim 3 wherein said system further comprises an enclosing wall positioned outside said chamber and having a first end surrounding said window, said wall establishing a volume and formed with an inlet to introduce said gas into said volume and an outlet to exhaust said gas from said volume.

6. A cleaning system as recited in claim 5 wherein said system further comprises a second window mounted in said enclosing wall and aligned to allow a laser beam to pass sequentially through said second window and said chamber window and enter said chamber.

7. A cleaning system as recited in claim 1 wherein said energy is electromagnetic radiation.

8. A cleaning system as recited in claim 7 wherein said subsystem comprises a microwave radiation emitter.

9. A cleaning system as recited in claim 7 wherein said electromagnetic radiation has a wavelength in the range of 1 mm to 3 cm.

10. A cleaning system as recited in claim 1 wherein the plasma comprises a plasma formation material, an etchant for the plasma formation material is introduced into the chamber, and the subsystem heats deposited plasma formation material on the inside surface of the window to a temperature greater than 150° C. to increase a rate of a chemical reaction between deposited plasma formation material and the etchant.

11. A cleaning system as recited in claim 10 wherein the plasma formation material comprises Sn.

12. A cleaning system as recited in claim 10 wherein the etchant is selected from the group of etchants consisting of HBr, $Br_2$, $Cl_2$, HCl, $H_2$ and combinations thereof.

13. A cleaning system as recited in claim 1 wherein the window is a laser input window.

14. A cleaning system as recited in claim 1 further comprising a conical shroud positioned in said chamber and having a first end surrounding said window and a second open end, said system further comprising a system for flowing a gaseous etchant in said shroud.

15. A cleaning system as recited in claim 1 wherein said window is made of a material selected from the group of materials consisting of fused silica, ZnSe, NaCl, KCl and $CaF_2$.

16. A cleaning system for a chamber window of an EUV light source, said light source utilizing a plasma formation material and generating debris by plasma formation, said system comprising;
   an etchant source to introduce an etchant for the plasma formation material into the chamber; and
   a heating subsystem directing heated gas toward said window to heat deposited plasma formation material on a surface of the window to a temperature greater than 150° C. to increase a rate of a chemical reaction between deposited plasma formation material and the etchant.

17. A cleaning system as recited in claim 16 wherein the plasma formation material comprises Sn and said etchant is selected from the group of etchants consisting of HBr, $Br_2$, $Cl_2$, HCl, $H_2$ and combinations thereof.

18. A cleaning system as recited in claim 16 wherein said window has an inside surface facing a chamber interior and an opposed outside surface and said heated gas is directed toward said outside surface of said window.

19. A cleaning system for a chamber window of a laser produced plasma EUV light source, said light source utilizing a plasma formation material and generating debris by plasma formation, said system comprising;
   a conical shroud positioned in said chamber and having a first end surrounding said window and a second open end;
   an etchant source to introduce an etchant for the plasma formation material into the shroud; and
   a heating subsystem directing radiation through said window to heat deposited plasma formation material on a surface of the window to a temperature greater than 150° C. to increase a rate of a chemical reaction between deposited plasma formation material and the etchant.

20. A cleaning system as recited in claim 19 wherein said heating subsystem comprises a plurality of microwave emitters.

21. A cleaning system as recited in claim 19 wherein said heating subsystem comprises source of non-focused laser radiation.

22. A cleaning system as recited in claim 19 wherein said heating subsystem heats deposited plasma formation material on the surface of the window to a temperature greater than 300° C.

23. A cleaning system as recited in claim 19 wherein said heating subsystem uniformly heats the surface of the window to a temperature greater than 300° C.

* * * * *